United States Patent [19]

Arntz et al.

[11] Patent Number: 5,171,898

[45] Date of Patent: Dec. 15, 1992

[54] METHOD FOR THE PRODUCTION OF 1,3-PROPANDIOL

[75] Inventors: Dietrich Arntz, Oberursel; Norbert Wiegand, Hanau, both of Fed. Rep. of Germany

[73] Assignee: Degussa Aktiengesellschaft, Frankfurt am Main, Fed. Rep. of Germany

[21] Appl. No.: 798,225

[22] Filed: Nov. 27, 1991

[30] Foreign Application Priority Data

Nov. 30, 1990 [DE] Fed. Rep. of Germany ....... 4038192

[51] Int. Cl.$^5$ .................. C07C 29/141; C07C 31/20; C07C 45/64; C07C 47/19
[52] U.S. Cl. ...................................... 568/862; 568/458
[58] Field of Search ................... 568/458, 862

[56] References Cited

U.S. PATENT DOCUMENTS 3,518,310  6/1970  Lutz ..................................... 568/458
3,536,763  10/1970  Eleuterio et al. ...................... 568/458
5,015,789  5/1991  Arntz et al. ........................... 568/862

*Primary Examiner*—Joseph E. Evans
*Attorney, Agent, or Firm*—Beveridge, DeGrandi & Weilacher

[57] ABSTRACT

The hydration of acrolein in the presence of a chelate-forming ion exchange resin based on polystyrene/divinyl benzene as catalyst and on the subsequent hydrogenation of the reaction mixture freed of the non-reacted acrolein and containing 3-hydroxypropionaldehyde is disclosed. As a result of using chelate-forming ion exchangers with anchor groups of the formula

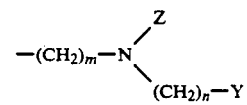

in which Z=H, $C_1$-$C_6$-alkyl, —$CH_2$—$CH(CH_3)$—Y' or —$(CH_2)_o$—Y' and Y and/or Y'=—COOH, —OH, pyridyl or —P(O)($CH_2OH$)OH, the hydration occurs at lower temperatures with a greater space-time yield and especially a greater selectivity than when using previously known ion exchangers. Resins with methylene imino diacetic acid anchor groups in the H form or partially doped with alkali-, alkaline-earth or earth-metal ions are especially suitable.

11 Claims, No Drawings

METHOD FOR THE PRODUCTION OF 1,3-PROPANDIOL

INTRODUCTION AND BACKGROUND

The present invention relates to a method of producing 1,3-propanediol by means of the hydration of acrolein in the presence of a chelate-forming ion exchange resin followed by subsequent catalytic hydrogenation of the 3-hydroxypropionaldehyde formed thereby.

It is known in the art that 1,3-propanediol has many possibilities of use as a monomeric structural element for making polyesters and polyurethanes and as the initial substance for the synthesis of cyclic compounds.

As is known from U.S. Pat. No. 2,434,110, acrolein can be hydrated in the presence of an acidic catalyst with the formation of 3-hydroxypropionaldehyde. The reaction preferably takes place at an elevated temperature using a solution of 5 to 30% by weight acrolein in water and an acid such as for example, sulfuric acid, phosphoric acid or acid salts of these acids as catalyst. The reaction mixture obtained during the hydration is optionally hydrogenated after removal of non-reacted acrolein in the presence of customary hydrogenation catalysts. Catalysts containing one or several metals which are effective in hydrogenation such as e.g. Fe, Co, Ni, Cu, Ag, Mo, W, V, Cr, Rh, Pd, Os, Ir, Pt are suitable for the hydrogenation of 3-hydroxypropionaldehyde to form 1,3-propanediol.

The low yields of 1,3-propanediol, which can be traced in particular to side reactions consuming acrolein during the hydration stage, are a disadvantage in the method of U.S. Pat. No. 2,434,110. Moreover, the selectivity of the hydration catalyzed by mineral acid is very dependent on the conversion of acrolein. In order to achieve an acceptable selectivity, the hydration is terminated at a low acrolein conversion with the disadvantage of a low space-time yield.

There has been no lack of attempts to reduce the disadvantages of the method evaluated above. For example, carboxylic acid esters of 3-hydroxypropionaldehyde are obtained by means of the attachment of lower carboxylic acids to acrolein by means of heating (U.S. Pat. No. 2,638,479) or in the presence of a basic ion exchange resin, which carboxylic acid esters can be hydrogenated to the corresponding esters of 1,3-propanediol. Disadvantages in these methods are the additionally necessary steps for the saponification of the ester and for the recycling of the carboxylic acid as well as the undesired formation of n-propanol and its carboxylic acid esters during the hydrogenation (DE-OS 20 57 399). The hydration of acrolein with carbon dioxide as catalyst is also known; however, this method requires long reaction times—see DE-OS 19 05 823.

It has been determined that the hydration of acrolein can be carried out using e.g. phosphoric acid or dihydrogen phosphates as catalyst but that problems occur in the subsequent hydrogenation if the hydroxypropionaldehyde solution obtained in this manner is hydrogenated without immediate separation of the hydration catalyst.

If nickel hydrogenation catalysts, which are actually very effective, are used, the catalyst is more rapidly deactivated upon repeated use of this catalyst than if a reaction mixture free of acid and salt is hydrogenated. This results in an elevated consumption of catalyst. In addition, the presence of the hydration catalyst during the workup by distillation causes product losses due to decomposition and, in the case of a preceding neutralization, in cloggings and encrustations in the system. Also, the elimination of distillation residues is more difficult given a content of inorganic salts and thus more expensive than is the case without these salts.

The indicated problems can be partially circumvented if the hydration catalyst is removed from the reaction mixture by ion exchangers before the hydrogenation or if 3-hydroxypropionaldehyde is separated by extraction from the reaction mixture and is then hydrogenated. However, both alternative measures for reducing the consumption of expensive hydrogenation catalyst necessitate additional apparatuses, and result in a greater expenditure of energy and in waste water problems and thus increase the production cost for 1,3-propanediol.

According to the method of U.S. Pat. No. 3,536,763, the hydration of acrolein is carried out at 40° to 120° C. in the presence of weakly acidic cation exchange resins whose functional groups are only carboxyl groups. Preferably, 0.1 to 5% of the functional groups should be present in the form of an alkali-, alkaline-earth- or earth-metal carboxylate. The yields of 3-hydroxypropionaldehyde are indicated at approximately 80% and the yields from the acrolein conversion in the range of 25 to 65% should be practically not dependent. This document also describes the known hydrogenation of 3-hydroxypropionaldehyde to 1,3-propanediol.

During the repetition of the method of U.S. Pat. No. 3,536,763, the catalytic activity of the ion exchange resins with carboxyl groups was able to be corroborated; however, the degree of the activity made the use of these ion exchangers in industrial systems appear to be unsuitable. It turned out that these catalysts require rather high temperatures and rather long reaction times, which runs contrary to the desired high space-time yield and high selectivity.

SUMMARY OF THE INVENTION

An object of the present invention is to provide available an improved method for the production of 1,3-propanediol by means of the hydration of acrolein in the presence of ion exchange resins with subsequent catalytic hydrogenation which can be carried out in the hydration stage with good selectivity and with the highest possible space-time yield. The reaction mixture obtained during hydration should also deactivate the hydrogenation catalyst as little as possible in order to make possible the reuse of the hydrogenation catalyst in subsequent batches and to lengthen the residence time of a fixed bed hydrogenation catalyst and thereby improve the economy of the method.

In carrying out the method of the invention for the production of 1,3-propanediol, the hydration of acrolein is conducted in the presence of an ion exchanger with the formation of 3-hydroxypropionaldehyde, during which hydration reaction acrolein and water are reacted in a weight ratio of 1:2 to 1:20 at 30° to 120° C. and at a pressure in a range of 1 to 20 bars. After formation of the 3-hydroxypropionaldehyde, the ion exchanger is separated, and, to the extent present, the non-reacted acrolein is separated from the reaction mixture. The subsequent catalytic hydrogenation of the 3-hydroxypropionaldehyde is conducted under known conditions in the liquid or the gaseous phase using conventional hydrogenation catalysts.

A feature of the invention resides in that chelate-forming ion exchangers are used which contain anchor groups bound to the polymer matrix of a polymerization resin and where the anchor groups are of the formula

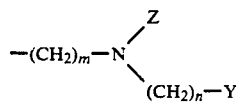

in which

Z is H, $C_1$- to $C_6$-alkyl, —$CH_2$—$CH(CH_3)$—Y' or —$(CH_2)_o$—Y';

Y and Y' are identical or different; —COOH, —OH, pyridyl or —P(O) ($CH_2OH$)OH, in which the acidic functional groups can in some cases be present in the form of their alkali-, alkaline-earth- or earth-metal salts, m is 0, 1, 2 or 3 n is 1, 2 or 3 for Y=—COOH, pyridyl or —P(O)($CH_2OH$)OH; 2 or 3 for y=—OH o is 1, 2 or 3 for Y'=—COOH, pyridyl or —P(O)($CH_2OH$)OH; 0, 2 or 3 for Y'=—OH.

Chelate-forming ion exchangers have been known for a long time. The book "Chelatbildende Ionenaustauscher" [German—Chelate-forming Ion Exchangers] by R. Hering, Akademie Verlag Berlin (1967) offers a survey of the structure, production, properties and use of such ion exchangers.

The polymer matrix (loc. cit., pages 25-58) of the polymerization resins is preferably based on a copolymerizate of styrene and divinyl benzene but can also be an acrylic polymer or copolymer of acrylic compounds and allyl compounds as well as be a polymer of a functionalized epoxide. The anchor groups can be introduced into the polymerization resins in a known manner into the polymer matrix, e.g. (a) by means of chloromethylation of the polymer with subsequent reaction with e.g. glycine, sarcosine, imino diacetic acid or imino dipropionic acid, ethanol amine, diethanol amine or ethanol amine monoacetic acid or (b) by means of nitration, reduction and reaction e.g. with chloroacetic acid. In individual instances a polymerizable monomer containing the anchor group can be polymerized in common with other monomers capable of copolymerization—note for example the copolymerization of N-allylimino dipropionic acid with acrylonitrile. Ion exchangers in which Y and/or Y' signify the group —(O)P(OH)$CH_2OH$ are known from EP-A 352,949 (GB 017051 of Aug. 18, 1988). Ion exchangers containing the picoyl amine groups are known from U.S. Pat. No. 4,031,038.

Macroporous polymerization resins based on styrene/divinyl benzene copolymers are used with preference; the amino group is preferably bound via a methylene group—m is thus 1 here—to the aromatic matrix. Especially suitable chelate-forming ion exchangers exhibit as anchor group the methylene imino diacetic acid group with n, m, o=1 and Z=$CH_2COOH$ and Y=-COOH and it is known that a certain amount of the anchor groups can consist of amino acetic acid functions, that is, m, n=1, Z=H and Y=—COOH.

The chelate-forming ion exchangers with at least one acid group in the anchor group can be used in the form of the free acid (H form); a part of the acid groups— especially up to one third of the total exchange capacity of the resin—can also be present in the form of an alkali-, alkaline-earth- or earth-metal salt. Ion exchangers whose acid groups are present essentially in the H form are especially preferred.

The conversion of an exchanger supplied in the Na form into the H form takes place in the manner customary for ion exchangers. The adjustment of a certain charge state with metal cations can take place from the H form by means of the addition of the appropriate amount of metal hydroxide, dissolved or suspended, in a suspension of the resin in water. However, an exchanger partially present in the H- and Na form can be obtained by means of the addition of an amount of acid to the Na form of the exchange resin which amount is not sufficient for a complete exchange of the Na ions. In both instances the ion exchange resin is freed of soluble salts and other soluble components before its use by means of washing with deionized water. The exchange capacity can be within a broad range. However, exchangers with a capacity in a range of approximately 1 to 3 equivalents (H form) per liter exchange resin have proven themselves to be especially suitable. The capacity is a measure for the density of the chelate-forming anchor groups in the exchange resin.

Among the ion exchangers in which Y and/or Y' signifies/signify the pyridyl group, those with anchor groups with the formula

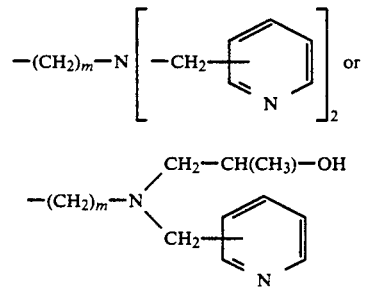

in which m signifies 0, 1, 2 or 3, especially 1, are preferred.

The ion exchangers to be used in accordance with the invention are generally distinguished by a high residence time. In order to obtain the highest selectivity and therewith the highest possible yield of 3-hydroxypropionaldehyde and to maintain it for a long operating time, it is recommended that one not strive for the highest possible acrolein conversion.

The hydration of acrolein can be carried out, as is apparent from patent application P 39 26 136.0 (not yet published), by means of using cation exchangers with phosphonic acid groups, especially chelate-forming amino phosphonic acid groups. According to said application P 39 26 136.0 and considering the unsatisfactory results obtained with ion exchangers containing carboxyl groups in accordance with U.S. Pat. No. 3,536,763, it could not have been expected that the chelate-forming cation exchangers containing carboxyl groups to be used with preference in accordance with the invention are excellently suited as catalysts for the hydration of acrolein. Moreover, the ability of chelate-forming anion exchangers to function as hydration catalysts also could not have been foreseen.

DETAILED DESCRIPTION OF THE INVENTION

In carrying out the invention acrolein and water are supplied in a weight ratio of 1:2 to 1:20, especially 1:3 to 1:10 and preferably 1:3 to 1:6 to the hydration stage. The reaction to 3-hydroxypropionaldehyde takes place in a temperature range of 30° to 120° C. A temperature in a range of 40° to 90° C. is preferred; a temperature below 40° C. generally results in long reaction times whereas a temperature above 90° C. results in a reduced selectivity and problems regarding the residence time of the exchange resins. It is especially preferable if the hydration takes place at 50° to 80° C.

In the temperature range below the boiling point of acrolein, the reaction can take place at normal pressure or at moderate pressure. In the case of reaction temperatures around or above the boiling point of acrolein, the work is performed under a pressure in a range of approximately 2 to 20 bars. In the preferred temperature range of 40° to 90° C., a pressure in a range of 2 to 5 bars has proven to be suitable.

The hydration is generally carried out up to an acrolein conversion in a range of 30 to 90% or above; a conversion of 40 to 90% and especially 50 to 80% is preferred.

Polymerization inhibitors such as hydroquinone, hydroquinone monomethylether or butylated phenols are advantageously added in an effective amount to the acrolein-water mixture.

The hydration can take place either discontinuously or continuously and known reactors such as agitator reactors, loop reactors, floating bed reactors, fluid bed reactors and fixed bed reactors can be used. The last-named reactors are preferred over loop reactors and agitator reactors. The flowthrough speed through a fixed bed reactor containing the chelate-forming ion exchanger and provided with a heatable jacket as well as the reaction temperature are preferably coordinated in such a manner with one another that the desired acrolein conversion is achieved with a single passage of the reaction mixture through the reactor.

After separation of the ion exchanger, which usually takes place by means of sedimentation or filtration or results by itself when using a resin bed (as is customary, for example, in water preparation), the reaction mixture is freed, to the extent necessary, of non-reacted acrolein. The separation of the acrolein can be realized in a known manner, especially by means of distillation, preferably under reduced pressure and temperatures below 80° C. The recovered acrolein can be fed back into the process after stabilization. The practically acrolein-free hydroxypropionaldehyde solution obtained can be reconcentrated before hydrogenation e.g. via a thin-layer evaporator.

The catalytic hydrogenation of the 3-hydroxypropionaldehyde in liquid phase is carried out in a known manner and in customary hydrogenation apparatus. The catalyst can be used in suspended form per se or carrier-bound or can be present in a fixed bed reactor; homogenous catalysts can also be used. Suitable suspension catalysts are Raney nickel, which can be doped with various other metals, as well as finely distributed platinum on a carrier material such as activated carbon. Among the fixed-bed catalysts, the substances cited in the evaluation of U.S. Pat. No. 2,434,110 are used; nickel catalysts have proven to be especially effective catalysts. In order to achieve a high conversion rate, the hydrogenation is carried out under pressure and at elevated temperature and the aqueous solution exhibits a pH in a range of 3.0 to 8.5, preferably around 6. Pressures of 20 to 250 bars, especially 40 to 150 bars, and temperatures of 40° to 140° C., especially 60° to 100° C., are preferred.

In principle, 3-hydroxypropionaldehyde can also be catalytically hydrogenated in the gas phase—see DE patent 20 54 601, so that this embodiment of hydrogenation can also follow the hydration of the invention.

As is apparent from the examples, it is possible to achieve a very high selectivity with a high acrolein conversion at the same time by means of using the chelate-forming ion exchangers of the invention as hydration catalyst. This makes it possible to carry out the hydration with a high space-time yield. The previously known, weakly acidic ion exchangers containing carboxyl groups result in much lower space-time yields on account of their lesser activity and lesser selectivity. The hydration of the invention results in reaction mixtures which can be readily freed of non-reacted acrolein and then be hydrogenated.

EXAMPLES 1 TO 5 AND COMPARATIVE EXAMPLES 1 TO 3

In order to determine the activity of ion exchangers according to the state of the art (comparative examples CE1 to CE3) and the present invention (examples 1 to 5), the following test is performed:

A 50 ml small septum bottle is filled with 25 ml ion exchanger catalyst and water is added until the catalysts is just covered. In addition, 16 g water and 7.56 g acrolein (Ac) are added. The mixture is agitated 3 minutes at room temperature by means of a rotating motion and the actual acrolein concentration of a specimen is determined by gas chromatography. The specimen is agitated further for 60 minutes in a water bath at the indicated temperature and analyzed. Table 1 shows the conversion and the selectivity after 1 hour reaction, the start concentration of acrolein and the reaction temperature.

A sharply acidic ion exchanger (CE1) results in a high acrolein conversion but in a totally insufficient selectivity. Only an average selectivity is obtained with the weakly acidic, non-chelate-forming ion exchanger (CE2) with an average conversion. A weakly acidic, $Ca^{2+}$-doped ion exchanger is more reactive but also only moderately selective. The exemplary chelate-forming ion exchangers with imino diacetic acid groups (examples 1 to 3) as well as the chelate-forming, basic ion exchangers of examples 4 and 5 are both very active and also very selective.

TABLE 1

|  | Catalyst Designation | Functional Grouping | Ac-start conc. (% by wt.) | Temperature °C. | One Hour Conversion (% by wt.) | Selection |
|---|---|---|---|---|---|---|
| CE 1 | ®Lewatit S 100* | —$SO_3H$ | 17.9 | 70 | 92.0 | 22 |
| CE 2 | ®Lewatit CNP 80* H-Form | —COOH | 15.1 | 70 | 21.6 | 49 |
| Ce 3 | ®Lewatit CNP LF,* H-Form, $Ca^{2+}$-Doped | —COOH ($Ca^{2+}$) | 15.7 | 70 | 43.4 | 50 |
| Example 1 | ®Amberlite** | Imino | 16.2 | 70 | 77.5 | 82 |

TABLE 1-continued

| | Catalyst Designation | Functional Grouping | | Ac-start conc. (% by wt.) | Temperature °C. | One Hour Conversion Selection (% by wt.) | |
|---|---|---|---|---|---|---|---|
| | IRC-718, H-Form | Diacetic Acid | | | | | |
| Example 2 | ®Duolite ES 466** H-Form | Imino Diacetic Acid | | 18.4 | 70 | 71.7 | 77 |
| Example 3 | ®Lewatit TP 208* H-Form | Imino Diacetic Acid | a b | 18.3 18.0 | 50 40 | 70.7 38.5 | 87 91 |
| Example 4 | ®DOWEX XFS*** 4195.02 | Bis-picolyl Amine | | 17.5 | 50 | 36.0 | 74 |
| Example 5 | ®DOWEX XFS*** 43084.00 | Hydroxy-propyl-picolyl Amine | | 16.5 | 50 | 39.6 | 84 |

*Bayer AG
**Rohm & Haas, Co.
***Dow Chemcial

EXAMPLES 6 TO 9

The hydration took place in accordance with the preceding examples. The ion exchanger of example 3 (Lewatit TP 208 H-form) was used, which was partially doped with metal ions by means of treatment with aqueous NaOH- (examples 6 and 7), $MgSO_4$—(example 8) or $Al(NO_3)_3$—solution (example 9). The degree of doping was determined by analyzing the resin specimens dried in a vacuum. The conditions and results follow from table 2; reaction temperature 50° C. It turned out that the ion exchangers partially doped with metal ions can be used up to very high conversions without decrease of selectivity.

TABLE 2

| Example | Doping % by wt. | Ac-conc. % by wt. | converion after 4 hours (% by wt.) | selectivity after 4 hours (% by wt.) |
|---|---|---|---|---|
| 6 | 0.53 Na | 17.7 | 90.5 | 82.8 |
| 7 | 4.2 Na | 17.2 | 89.1 | 85.1 |
| 8 | 0.06 Mg | 17.7 | 89.3 | 80.4 |
| 9 | 0.3 Al | 17.8 | 88.9 | 81.1 |

EXAMPLE 10

The hydration of acrolein is carried out continuously for a rather long time in a laboratory apparatus with a fixed bed reactor with ion exchange resin as catalyst. Conversion and selectivity are determined by analyzing the product solution.

The apparatus consists of a graduated, coolable 2 liter glass vessel for the aqueous initial acrolein solution, an HPLC pump for transporting the reaction mixture, a thermostated, pressure-resistant, precision ground glass tube (300 mm×26 mm in diameter) which receives the ion exchange filling and is closed at both ends with adjustable screw caps, a pressure resistance valve, a 2 liter glass receiver cooled to +5° C. for the product and of the necessary thermostatting devices.

The acrolein-water mixture, cooled to +5° C., is placed in a receiver and pumped by the HPLC pump through the fixed bed of 138 ml ion exchange resin maintained at reaction temperature at a constant volumetric flow. After a break-in period of 3-5 h for adjusting the stationary state, acrolein solutions are pumped through the thermostated glass tube, after having replaced the receiver, under constant test conditions for a period of several hours. This measurement is repeated several times. The product solutions obtained in each instance are analyzed by gas chromatography-see table 3.

| Ion exchanger used: | ®Lewatit TP 208 (Bayer AG) H-form |
|---|---|
| Acrolein start concentration: | 16.9 % by wt. |
| Reaction temperature: | 60° C. |
| LHSV (= liquid hourly space velocity): | 0.54 hour$^{-1}$ |

TABLE 3

| Operating time (hours) | Conversion (%) | Selectivity (%) |
|---|---|---|
| 40 | 86 | 78 |
| 80 | 82 | 82 |
| 120 | 78 | 80 |

EXAMPLE 11

The hydration of the acrolein takes place in the manner described in example 10. The Lewatit TP 208 (H-form) (Bayer AG) ion exchanger was used; Reaction temperature 50° C.; initial concentration of the aqueous acrolein solution 16.9% by weight; LHSV=0.53 h$^{-1}$. Within an operating time of 200 hours, the selectivity was consistently at 80%.

EXAMPLE 12

Hydrogenation of an aqueous solution of 3-hydroxy-propionaldehyde (HPA) obtained according to example 11 on a fixed-bed contact (Ni/$Al_2O_3$/$SiO_2$).

The reaction solution of example 11 is freed at 65° C. and under reduced pressure of non-reacted acrolein and of a part of the water at the same time. 750 ml of an aqueous solution containing 1.43 moles HPA and with a pH of 5 are introduced into the hydrogenation reactor of a customary design and circulated over 140 g catalyst. The hydrogenation is performed for 4 hours at 55° C. at an $H_2$ pressure of 150 bars which drops during the hydrogenation to 105 bars. The HPA conversion is 100% and the yield of 1,3-propanediol 81% (quantitative gas chromatography). The workup of the reaction solution takes place by means of distillation in a known manner.

The HPA conversion and the yield of 1,3-propanediol remain essentially high and unchanged, even given repeated usage of the hydrogenation catalyst.

EXAMPLE 13

Hydrogenation of an aqueous solution of 3-hydroxypropionaldehyde (HPA) obtained according to example 11.

The reaction solution of example 11 is freed of non-reacted acrolein via a distillation column at 500 mbars. The aqueous HPA solution obtained is then further concentrated by evaporation on a thin-layer evaporator at a jacket temperature of 100° C. and a pressure of 200 mbars. 500 g of the 19% by weight solution obtained in this manner are hydrogenated in a 1000 ml autoclave with gassing agitator at 135 bars hydrogen pressure at a temperature of 75° C. and an agitator speed of 1000 rpms in the presence of 5.8 g Raney nickel at pH 7 within 60 min. The HPA conversion is 99.9% and the yield of 1,3-propanediol 81% relative to acrolein used. The workup of the reaction solution takes place by means of distillation in a known manner.

As used herein, the term "earth metal" is intended to designate the elements Al, Sc, Y, La and the 14 lanthanides; see Roeupps Chemie-Lexikon 1976.

Further variations and modifications of the foregoing invention will be apparent to those skilled in the art and are intended to be encompassed by the claims appended hereto.

German priority application No. P 40 38 192.7 is relied on and incorporated herein by reference.

We claim:

1. A method for the production of 1,3-propanediol by hydration of acrolein in the presence of an ion exchanger with formation of 3-hydroxypropionaldehyde, comprising reacting acrolein and water in a weight ratio of 1:2 to 1:20 at 30° to 120° C. and a pressure in a range of 1 to 20 bars, in the presence of an ion exchanger to form a reaction mixture, separating said ion exchanger and any non-reacted acrolein from said reaction mixture, and subsequently catalytically hydrogenating the 3-hydroxypropionaldehyde in liquid or gaseous phase in the presence of a hydrogenation catalyst, wherein said ion exchanger is a chelate-forming ion exchanger which contains at least one anchor group bound to the polymer matrix of a polymerization resin, said anchor group having the formula

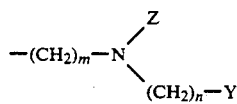

in which
Z is H, $C_1$- to $C_6$-alkyl, $-CH_2-CH(CH_3)-Y'$ or $-(CH_2)_o-Y'$;
Y and Y' are identical or different; $-COOH$, $-OH$, pyridyl or $-P(O)(CH_2OH)OH$, in which the acidic functional groups can partially be present in the form of their alkali-, alkaline-earth- or earth-metal salts,
m is 0, 1, 2 or 3
n is 1, 2 or 3 for Y=$-COOH$, pyridyl or $-P(O)(CH_2OH)OH$; 2 or 3 for Y=$-OH$
o is 1, 2 or 3 for Y'=$-COOH$, pyridyl or $-P(O)(CH_2OH)OH$; 0, 2 or 3 or Y'=$-OH$.

2. The method according to claim 1, wherein said chelate-forming ion exchanger comprises methylene imino diacetic acid anchor groups or methylene imino dipropionic acid anchor groups.

3. The method according to claim 2, wherein a part of the carboxyl groups is present in the form of alkali-, alkaline-earth- or earth-metal carboxylates.

4. The method according to claim 1, wherein said anchor group is of the formula

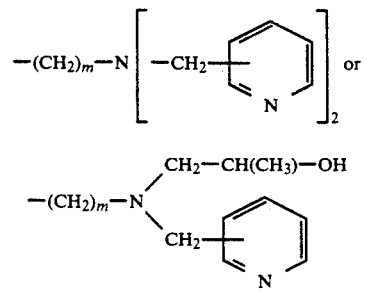

in which m is 0, 1, 2 or 3, preferably 1.

5. The method according to claim 4, wherein m is 1.

6. The method according to claim 1, wherein acrolein and water are used in a weight ratio of 1:3 to 1:10.

7. The method according to claim 1, wherein said C. hydration reaction is carried out at 40° to 90° C.

8. The method according to claim 1, wherein the hydration is operated up to an acrolein conversion of 30 to 90%, the ion exchanger is subsequently separated and then non-reacted acrolein is distilled off from the aqueous reaction mixture for return into the hydration stage.

9. The method according to claim 1, wherein the ion exchanger is located in a fixed bed reactor and the volume of the fixed bed as well as the flowthrough and the reaction temperature are coordinated with each other in such a manner that the desired acrolein conversion is achieved with a single passage of the reaction mixture through the reactor.

10. The method according to claim 1, wherein the catalytic hydrogenation of the 3-hydroxypropionaldehyde is carried out in aqueous solution under pressure at 20 to 250 bars in a temperature range of 40° to 140° C. and in a pH range of 3.0 to 8.5.

11. The method according to claim 1, wherein the hydrogenation of 3-hydroxypropionaldehyde is carried out in the presence of suspension bed or fixed bed catalysts containing nickel or noble metal.

* * * * *